United States Patent [19]
Kralovic

[11] Patent Number: 6,103,189
[45] Date of Patent: Aug. 15, 2000

[54] METHOD OF REMOVING MICROBIAL CONTAMINATION

[76] Inventor: Raymond C. Kralovic, 9121 Brakeman Rd., Hambden Township, Ohio 44024

[21] Appl. No.: 09/037,639

[22] Filed: Mar. 10, 1998

[51] Int. Cl.$^7$ ........................................................ A61L 2/18
[52] U.S. Cl. ................................. 422/28; 422/37; 134/26; 134/3; 134/22.1; 134/22.14; 134/22.19; 134/41; 134/28; 134/27; 134/29
[58] Field of Search ........................... 422/28, 37; 134/26, 134/3, 22.1, 22.14, 22.19, 41, 28, 27, 29

[56] References Cited

U.S. PATENT DOCUMENTS

| | | |
|---|---|---|
| 4,721,123 | 1/1988 | Cosentino et al. . |
| 4,731,222 | 3/1988 | Kralovic et al. . |
| 4,892,706 | 1/1990 | Kralovic et al. . |
| 5,037,623 | 8/1991 | Schneider et al. . |
| 5,077,008 | 12/1991 | Kralovic et al. . |

*Primary Examiner*—Robert J. Warden, Sr.
*Assistant Examiner*—Jennifer C. McNeil
*Attorney, Agent, or Firm*—Locke Liddell & Sapp LLP

[57] ABSTRACT

Medical instruments, such as endoscopes, may be sterilized or disinfected in a liquid chemical sterilant (LCS). The LCS is of sufficient potency to sterilize the contaminated medical device. In addition it is self-degrading, non-contaminating, and non-corrosive. It does not require the addition of chemically contaminating anti-corrosive compounds and detergents. Preferred LCS for use in the invention include peracetic acid, silver activated hydrogen peroxide and acidic sodium hypochloride. A particularly preferred LCS is peracetic acid since it has particular applicability with plastic components of medical devices.

20 Claims, No Drawings

METHOD OF REMOVING MICROBIAL CONTAMINATION

SPECIFICATION

1. Field of the Invention

The invention relates to a method of using a liquid chemical sterilant in the sterilization or disinfection of medical instruments. The method of the invention makes unnecessary the use of a rinse sterilant.

2. Background of the Invention

U.S. Pat. Nos. 4,731,222 and 4,992,706 disclose a method of using a liquid chemical sterilant (LCS) to sterilize contaminated medical devices. The contaminated medical device is enclosed in a module. The LCS containing composition is then introduced from a reservoir into the module. The LCS composition is allowed to remain in contact with all internal surfaces, including those of inclused medical instruments or devices for a time, temperature and LCS concentration sufficient to effect sterilization or disinfection by applicable regulatory standards. The LCS composition is discharged after sterilization. A sterile rinse fluid is subsequently introduced into the module. An aqueous rinse fluid, which may be produced by passing tap water or other rinse solution through a sterilization filter, removes the anti-microbial composition from the module and medical instruments or devices. The pathway from the anti-microbial composition reservoir to the module is first sterilized in its entirety by the LCS composition prior to the introduction of the sterile rinse fluid. As such, there is no potential for the pathway to be exposed to a contaminant at the time of introduction of the sterile rinse fluid.

In theory, only the LCS composition is needed to sterilize the medical device. It would be highly desirable to employ a sterilizing fluid which did not require the additional step of a sterile rinse fluid. The elimination of a sterile rinse fluid from the process would decrease the time required to complete sterilization. In addition, it would make the sterilization process less complex and costly. It would also eliminate the potential of recontaminating sterilized medical devices with waterborne viruses. When sterilizing filters are used, it is well known that such viruses can pass through such filters.

A LCS composition which does not require a sterile rinse fluid must be of sufficient potency and sterilizing ability to sterilize medical devices. In addition, it needs to be self degrading, non-contaminating and non-corrosive without the addition of chemically contaminating anticorrosive compounds and detergents.

SUMMARY OF THE INVENTION

The invention relates to a method of removing microbial contamination by use of a liquid chemical sterilant which does not require a sterile rinse fluid. Examples of suitable sterilants for use as LCS in the invention include peracetic acid, silver activated hydrogen peroxide and acidic sodium hypochloride. Solutions of peracetic acid have been found to be particular applicable in the sterilization of medical devices composed of plastic materials.

The method of the invention has particular applicability in the sterilization of endoscopes.

DETAILED DESCRIPTION OF PREFERRED EMBODIMENTS

Medical instruments, which may contain brass, copper, aluminum, stainless steel, carbon steel or plastic components, may be sterilized or disinfected in an anti-microbial composition. Such instruments include, but are not restricted to, endoscopes, forceps, scissors, tongs or any other instrument which comes into contact with the human body. The invention particularly relates to the disinfection or sterilization of endoscopes.

It has been found that a LCS composition to sterilize medical devices, without the possibility of recontamination, may be achieved by the use of an LCS composition that is self-removing and self-sterilizing. In other words, the LCS composition is capable of chemical degradation or removal by evaporation and drying. No sterile rinse solution is therefore required.

The LCS composition employed in the invention is of sufficient potency, i.e. sterilizing ability, to sterilize contaminated medical devices. In addition, it is self-degrading, non-contaminating and non-corrosive. It does not require the addition of chemically contaminating anti-corrosive compounds and detergents.

Typically, the amount of LCS present in the LCS composition is between from about 0.005 weight percent to about 1.0 weight percent per volume.

Preferred LCS for use in the invention include oxygen releasing compounds such as peracetic acid, organic peroxides, hydrogen peroxide and inorganic peroxides and chlorine, chlorine dioxide, active chlorine releasing compounds such as chloramines and hypochlorites. Particularly preferred are peracetic acid, silver activated hydrogen peroxide and acidic alkali or alkaline earth hypochloride such as acidic sodium hypochloride, calcium hypochloride and lithium hypochloride. The peracetic acid is preferably alkaline when employed. An especially preferred LCS is peracetic acid since it has particular applicability with plastic medical devices.

A peracetic acid containing solution most desirably has a pH less than or equal to 3.0. The solution is destablized at a pH greater than or equal to 7.0. The pH of a destabilized LCS composition containing hypochlorites preferably is less than or equal to 7.0. At a pH in excess of 10.0, such LCS containing compositions are stable and less active. A LCS composition containing hydrogen peroxide has a pH upon activation less than or equal to 6.0. It can be inactivated by drying or the addition of a minute amount of catalyst capable of decomposing hydrogen peroxide such as catalase. Such peroxide decomposition catalysts are well known in the art.

In one embodiment of the invention, after the contaminated medical instrument is placed into the sterilization chamber, the medical instrument is (first) decontaminated with an anti-microbial composition which may optionally contain buffers, detergents and/or corrosion inhibitors. Wetting, agents may further be employed and, where tap water is used as diluent, a sequestering agent (such as sodium hexametaphosphate) may also be used to prevent the precipitation of calcium and magnesium salts. The sequestering agent is not necessary where either deionized or soft water is utilized.

Corrosion inhibitors may be desired where the medical instrument contains some or all parts composed of such metals as copper, brass, aluminum or steel. The amount of corrosion inhibitor typically employed in the anti-microbial composition of the invention is between from about 0.005 to about 0.1 weight percent by volume. Copper and brass corrosion inhibitors may be selected from the group consisting of triazoles, azoles, benzoates and five membered ring compounds. Triazoles, especially benzotriazole and tolytriazole, are typically preferred. Aluminum and steel corrosion inhibitors, as well as buffering, agents, may be selected from the group consisting of chromates, dichromates, borates, phosphates, molybdates, vanadates, silicates, and tungsdates. Typically, phosphates are employed to inhibit steel corrosion and to buffer the anti-microbial composition to the desired pH. Molybdates are typically preferred for inhibiting aluminum corrosion. The amount of buffering agent typically employed in the anti-microbial composition is between from about 0.2 to about 12 weight percent per volume.

The anti-corrosive buffering compounds are preferably a mixture of phosphate in sufficient volume to produce a final concentration of 1.25 weight percent per volume and molybdates in an appropriate amount to produce a final solution of 0.011 weight percent per volume. Phosphates may also be effective in the range of 0.2 to 12 weight percent per volume and the molybdates may be effective from 0.1 to 10 weight percent per volume. Optionally, borates, chromates, dichromates, silicate tungsdates, vanadates and combinations thereof, may be substituted in appropriate concentrations to inhibit steel corrosion, buffer to a generally neutral pH, and/or inhibit aluminum corrosion. The objective of use of the compound as buffering agent is to increase the pH of the solution to greater than about 7.0. At this point, the LCS rapidly degrades to oxygen and volatile components. Where the LCS is peracetic acid, the LCS degrades to volatile acetic acid and oxygen.

The wetting agent is generally present in the anti-microbial composition in an amount from about 0.001 to about 0.05 weight percent per volume. The wetting agent serves to improve the wetting of the surface of the instrument by the anti-microbial composition.

When necessary, the amount of sequestering agent employed is between about 0.002 to about 0.10 weight percent per volume.

The LCS containing composition of the invention may further include a detergent compatible with strong oxidizers such as Dowflax 2A1. The amount of detergent in the anti-microbial composition of the invention is typically between from about 0.002 to about 0.10 weight percent by volume.

In the second step of one embodiment of the invention, the LCS composition is drained and removed from the sterilization chamber. A second, more dilute, solution of LCS containing composition, which may optionally contain a low concentration of a non-chemically contaminating, non-phosphate alkaline buffering compound may then be employed. Once again, as in the example employing peracetic acid, the buffering compound serves to increase the pH of the solution to greater than about 7.0 at which point the LCS rapidly degrades to oxygen and volatile components.

The second LCS containing composition is generally free of anti-corrosive compounds and detergents as well as sequestering and wetting agents. A sterile water rinse is therefore unnecessary. The rinse agent employed in the method of the invention is non-polluting. Use of sterile filters is not necessary. The primary requirement is that any remaining LCS is either non-toxic (e.g., by degradation) or can be removed by evaporation during drying of the sterilization chamber, if so desired.

The concentration of LCS in this second addition of LCS composition, while being sufficient to be self-sterilizing is at a lower concentration than in the first addition discussed above. This is the case since only the tap water bioburden (defined as the total amount of soil and microrganisms in the tap water that represents the sterilization challenge that must be destroyed by the dilute LCS) needs to be sterilized; the bioburden from the contaminated medical device having been sterilized by the first sterilant. Generally, the amount of LCS in the second addition of anti-microbial composition is between from about 1.0 to about 10.0 weight percent by volume of the first LCS composition.

The LCS in the second composition may be any of the referenced LCS's from the first composition. Typically, the same LCS is used in the first as well as second compositions. However, this is not necessarily the case.

It is possible that only a single addition of LCS composition may be used, provided the single composition is of sufficient potency (sterilizing ability) to sterilize the contaminated medical device, while being self-degrading, non-contaminating and non-corrosive and not require the addition of chemically contaminating anti-corrosive compounds and detergents. Peracetic acid is particularly desirable in such instances since it is capable of sterilizing naturally compatible devices constructed of plastic.

It is most desirable that the LCS containing composition (s) of the invention be practiced in a fully wetable sterilization chamber wherein all surfaces are equally exposed to the LCS. Suitable sterilization chambers are disclosed in the literature. See, for example, U.S. Pat. Nos. 4,731,222; 4,892, 706; and 5,037,623.

The sterilization chamber further should contain a means whereby sterilant solutions may be introduced into the sterilization chamber as well as means for draining sterilant solutions without compromising the sterility of the chamber or its ability to be sterilized as described herein.

Further, the sterilization chamber preferably has means whereby the LCS may be diluted and mixed. Alternatively, these processes may be performed prior to introduction to the sterilization chamber.

The following example will illustrate the practice of the present invention in its preferred embodiment. Other embodiments within the scope of the claims herein will be apparent to one skilled in the art from consideration of the specification and practice of the invention as disclosed herein. It is intended that the specification, together with the examples, be considered exemplary only, with the scope and spirit of the invention being indicated by the claims which follow.

EXAMPLE

A contaminated medical device is placed in sterilization chamber. If needed, the contaminated medical device is further connected to manifolds to expose the internal instrument lumens. An anti-microbial composition containing the following composition:

| Ingredient | Weight percentage by Volume in LCS Solution | Function |
| --- | --- | --- |
| Peracetic Acid | 0.2% | Active Biocide |
| Sodium Phosphate | 0.50 | Buffer |
| Benzotriazole | 0.02 | Anticorrosive |
| Dowflax 2A1 | 0.01 | Detergent/Wetting Agent | was then added to remove gross contaminants from the contaminated medical device. The anti-microbial solution is flushed and circulated over the external and internal surfaces of the contaminated instrument for a time at elevated temperature to produce sterilization and then flushed to the drain.

After the first treatment with the anti-microbial composition, the chamber is completely filled with the second anti-microbial composition composed of the following:

| Ingredient | Weight percentage by Volume | Function |
|---|---|---|
| Peracetic Acid | 0.01% | Active |
| Buffer | 0.02% | pH Adjustment | and allowed to remain in contact with all surfaces for a time at elevated temperature to produce sterilization of the bioburden in the tap water. The second anti-microbial composition is then drained from the chamber. The decontaminated medical instrument may then be removed from the sterilization chamber or dried prior to removal.

What is claimed is:

1. A method of removing and destroying microbial contamination from a medical instrument without a sterile water rinse, which comprises:
    mixing a first solution comprising a liquid chemical sterilant and water and, optionally, corrosion inhibitor, buffering agent, sequestering agent and/or wetting agent;
    circulating the first solution over all surfaces of the contaminated medical instrument until the instrument has been microbially decontaminated; and
    circulating a second solution free of anti-corrosive compounds and detergents and comprising liquid chemical sterilant and water over all surfaces of the contaminated medical instrument wherein the concentration of the liquid chemical sterilant in the second solution is less than the concentration of the liquid chemical sterilant in the first solution and free of nondecomposing chemical contaminates.

2. The method of claim 1, wherein the contaminated medical instrument is composed of brass, copper, aluminum stainless steel, carbon steel or plastic components.

3. The method of claim 2, wherein the contaminated medical instrument is an endoscope.

4. The method of claim 1, wherein the liquid chemical sterilant of the first solution and the second solution is selected from the group consisting of peracetic acid, silver activated hydrogen peroxide and an alkali or alkaline earth metal hypochloride.

5. The method of claim 4, wherein the liquid chemical sterilant in the first and second solutions is the same.

6. The method of claim 5, wherein the liquid chemical sterilant is peracetic acid.

7. The method of claim 4, wherein the liquid chemical sterilant in the first solution is peracetic acid.

8. The method of claim 4, wherein the liquid chemical sterilant in the second solution is peracetic acid.

9. The method of claim 1, wherein the first solution contains a buffering agent and/or corrosion inhibitor.

10. The method of claim 9, wherein the first solution further contains a wetting agent and a sequestering agent.

11. The method of claim 1, wherein the amount of liquid chemical sterilant in the first solution is between about 0.005 to about 1.0 weight percent per volume.

12. A method of removing and destroying microbial contamination from a medical instrument without a sterile water rinse consisting essentially of:
    mixing a solution comprising a liquid chemical sterilant and water and buffering agent; and
    circulating the solution over all surfaces of the contaminated medical instrument until the instrument and all connecting surfaces have been microbially decontaminated.

13. The method of claim 12, wherein the contaminated medical instrument is composed of brass, copper, aluminum, stainless steel, carbon steel or plastic components.

14. The method of claim 13, wherein the contaminated medical instrument is an endoscope.

15. The method of claim 12, wherein the amount of liquid chemical sterilant in the anti-microbial composition is between from about 0.005 to about 0.50 weight percent by volume.

16. The method of claim 12, wherein the liquid chemical sterilant is selected from the group consisting of peracetic acid, silver activated hydrogen peroxide and acidic sodium hypochloride.

17. The method of claim 16, wherein the liquid chemical sterilant is peracetic acid.

18. A method of removing and destroying microbial contamination from a medical instrument in the absence of a sterile water rinse which comprises mixing a solution comprising a liquid chemical sterilant selected from the group consisting of peracetic acid, organic peroxides, hydrogen peroxides, inorganic peroxides, chlorine, chlorine dioxide and active chlorine releasing compounds and water and circulating the solution over the surface of the contaminated medical instrument until the instrument has been microbially decontaminated.

19. The method of claim 18, wherein the liquid chemical sterilant containing solution further contains at least one member selected from the group consisting of corrosion inhibitors, buffering agents, sequestering agents and/or wetting agents.

20. The method of claim 18, further comprising circulating a second solution consisting essentially of liquid chemical sterilant and water over the surface of the contaminated medical instrument wherein the concentration of the liquid chemical sterilant in the second solution is less than the concentration of the liquid chemical sterilant in the first solution and free of nondecomposing chemical contaminates.

* * * * *